United States Patent
Kipke et al.

[11] Patent Number: 5,908,296
[45] Date of Patent: Jun. 1, 1999

[54] DENTAL AIR-WATER SYRINGE WITH WATER PURIFYING DEVICE

[75] Inventors: Cary A. Kipke, Woodbury; Raymond M. Gleason, Eagan, both of Minn.

[73] Assignee: Minnesota Mining & Manufacturing Co., St. Paul, Minn.

[21] Appl. No.: 08/991,470

[22] Filed: Dec. 16, 1997

[51] Int. Cl.⁶ .................................................. A61C 1/10
[52] U.S. Cl. ............................................................ 433/80
[58] Field of Search ................................. 433/80, 82, 84, 433/85, 86, 88

[56] References Cited

U.S. PATENT DOCUMENTS

| | | | |
|---|---|---|---|
| 3,593,423 | 7/1971 | Jones et al. | 433/80 |
| 3,698,088 | 10/1972 | Austin, Jr. | 433/80 |
| 3,923,665 | 12/1975 | Lambert et al. | 210/501 |
| 4,059,522 | 11/1977 | Polley et al. | 210/198 |
| 4,470,812 | 9/1984 | Martens et al. | 433/85 |
| 4,741,697 | 5/1988 | Herbison | 433/25 |
| 4,743,229 | 5/1988 | Chu | 604/82 |
| 4,888,118 | 12/1989 | Barnes et al. | 210/668 |
| 4,950,159 | 8/1990 | Hansen | 433/80 |
| 4,950,160 | 8/1990 | Karst | 433/88 |
| 4,961,698 | 10/1990 | Vlock | 433/86 |
| 4,973,247 | 11/1990 | Varnes et al. | 433/85 |
| 4,978,297 | 12/1990 | Vlock | 433/88 |
| 5,024,600 | 6/1991 | Kline | 433/82 |
| 5,192,206 | 3/1993 | Davis et al. | 433/80 |
| 5,204,004 | 4/1993 | Johnston et al. | 210/651 |
| 5,208,933 | 5/1993 | Lustig et al. | 15/22.1 |
| 5,230,624 | 7/1993 | Wolf et al. | 433/82 |
| 5,236,356 | 8/1993 | Davis et al. | 433/80 |
| 5,242,300 | 9/1993 | Esrock | 433/80 |
| 5,252,067 | 10/1993 | Kakimoto | 433/129 |
| 5,286,065 | 2/1994 | Austin et al. | 285/23 |
| 5,306,146 | 4/1994 | Davis et al. | 433/80 |
| 5,370,534 | 12/1994 | Wolf et al. | 433/80 |
| 5,474,451 | 12/1995 | Dalrymple et al. | 433/80 |
| 5,489,205 | 2/1996 | Davis et al. | 433/80 |
| 5,556,279 | 9/1996 | Wolf et al. | 433/82 |

FOREIGN PATENT DOCUMENTS

| | | |
|---|---|---|
| 0 661 024 A2 | 7/1995 | European Pat. Off. . |
| 28618 | 3/1925 | France ................................ 433/80 |
| 572365 | 3/1925 | France . |
| 2 213 732 | 8/1989 | United Kingdom . |
| WO 91/03986 | 4/1991 | WIPO . |

*Primary Examiner*—John J. Wilson
*Attorney, Agent, or Firm*—James D. Christoff

[57] ABSTRACT

A dental air-water syringe includes a handle and a tip as well as a device for purifying water flowing through the tip. In one embodiment of the invention, the water purifying device is contained within a housing of the tip and optionally includes a number of iodide beads disposed along the length of the housing. In another embodiment of the invention, the device is detachably connected to the tip, and the tip and the device have outer diameters that are approximately equal.

13 Claims, 2 Drawing Sheets

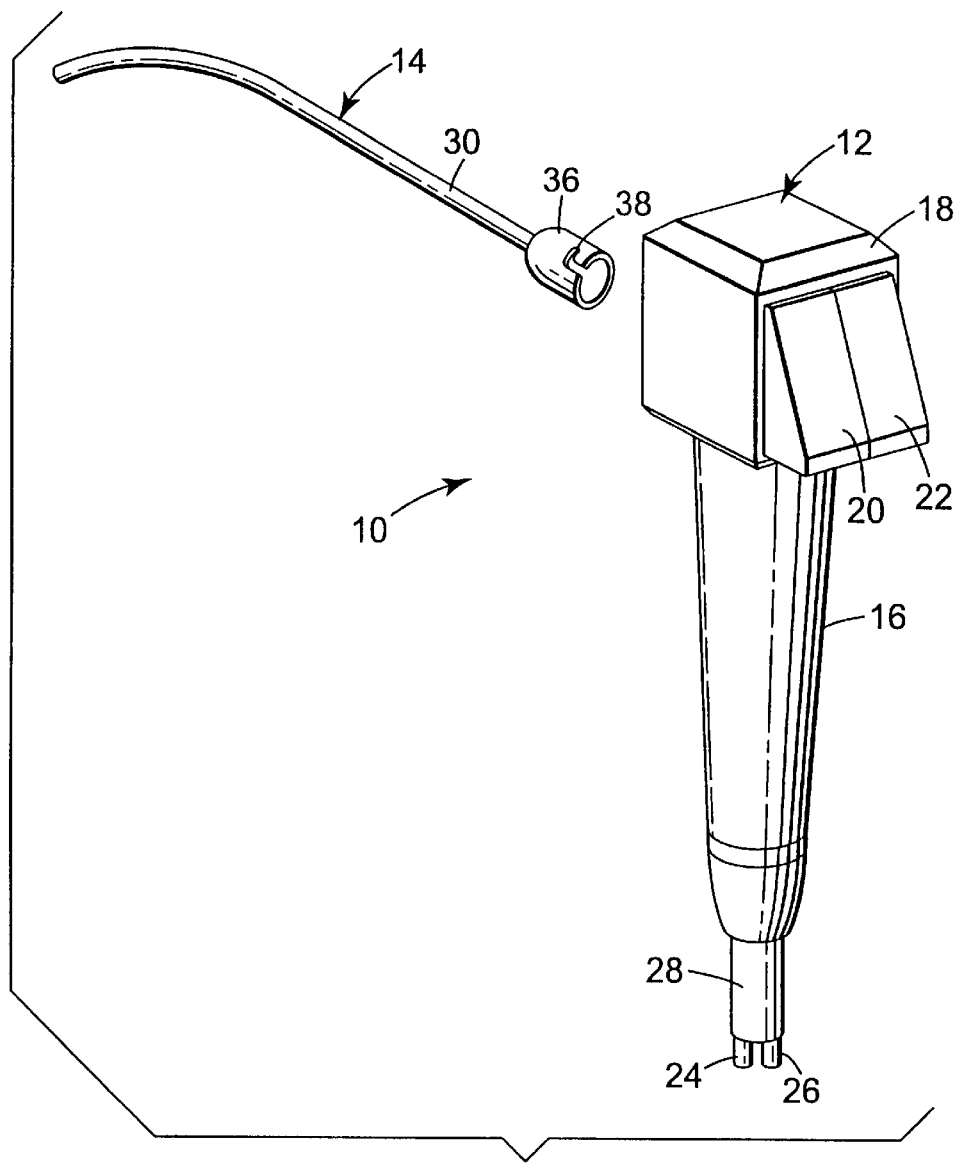
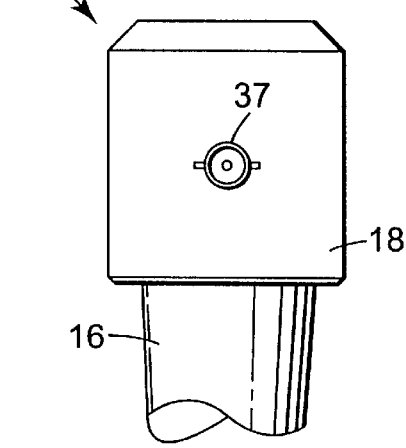

DENTAL AIR-WATER SYRINGE WITH WATER PURIFYING DEVICE

BACKGROUND OF THE INVENTION

1. Field of the Invention

This invention broadly relates to a dental syringe for dispensing air and/or water during dental procedures. More particularly, the invention relates to a dental air-water syringe having a replaceable device for purifying water flowing through the syringe.

2. Description of the Related Art

Hand-held syringes that dispense air and water are commonly used during many dental procedures. For example, compressed air dispensed from dental air-water syringes is often used to dry the patient's tooth structure such as the dentin or enamel. Many dental compositions do not bond strongly to tooth structure if water is present. The application of compressed air to the tooth surface provides a convenient, inexpensive means to assure that the tooth structure is essentially free of moisture so that a strong bond between the composition and the tooth structure is developed.

Water is often dispensed from dental air-water syringes to clean debris and other foreign matter that may be present in the oral cavity. As an example, a spray of water can be utilized to clean tooth structure that is to be subsequently dried by compressed air before ultimately receiving a dental material such as a restorative or the like. A spray of water in the patient's oral cavity can also help to eliminate objectionable odors during the dental procedure.

Dental syringes are typically connected to a source of air and a source of water by flexible tubing having separate air and water conduits. The tubing is often relatively long and has a relatively small cross-sectional area in order to allow the syringe to be held in a number of different orientations and facilitate maneuverability of the tip of the syringe in the oral cavity as may be needed.

Unfortunately, it has been found that film-like growths of microorganisms, also known as biofilms, are often present in large concentrations in the water conduit of the flexible tubing connected to dental air-water syringes. Such biofilms are microbial populations that typically include bacteria, fungi and protozoa that form on the inner surfaces of the small-diameter water conduit. Water flowing through the water conduit may pick up and transport microorganisms from the biofilm and consequently develop a bacterial count significantly higher than a bacterial count that is considered normally acceptable for potable water.

Water having a high bacterial count that is dispensed from dental air-water syringes is a cause for concern for both dental patients and dental staff, particularly if the patient or staff member has a relatively weak immune system. For example, many dental procedures may cause bleeding in the patient's oral cavity, and such bleeding increases the risk that bacteria from the biofilm will enter the patient's blood stream. The dental staff may also be exposed to risk of infection because the bacteria-laden water discharged from the syringe may disperse into the atmosphere as an aerosol and then inhaled.

A number of suggestions have been made in the past to reduce microbial population counts in water dispensed from dental instruments including air-water syringes and dental handpieces. One such suggestion concerned a filter having relatively small openings through which the water must pass before being dispensed from a syringe. An example of such a filter is described in U.S. Pat. No. 5,204,004 and includes a microporous membrane having a porosity that blocks the passage of particulate matter having a diameter larger than about 0.2 microns.

Another approach to reducing microbial population counts in water dispensed from dental instruments involves the use of disinfectant media. For example, U.S. Pat. No. 5,474,451 describes dental water dispensing instruments that include a disinfectant media held on a support. This patent describes media comprised of multi-valent iodine resin, as well as media made of a multi-valent iodine resin with bromide, a bromide derivative particulate, quantenary ammonium-silver-chlorine-bromine-bromide bearing medias, and other halogen resins or halogen derivatives.

Another method to reduce microbial population counts in water dispensed from dental instruments involves the use of chemical disinfection wherein a liquid that includes a chemical disinfectant is introduced into the instrument. As one example, the water passageways in the flexible tubing interconnecting the instrument and a source of water may be filled with a disinfectant solution that resides in the water conduit for about 10 minutes. The chemical disinfectant is then purged by tap water from the passageways prior to use of the instrument for dental applications. As another example, a dental instrument is connected to a source of disinfectant solution, and small but measurable amounts of the disinfectant solution are released into the water solution and are present in the discharged water.

Devices for reducing microbial population counts in water dispensed from dental air-water syringe water lines, including the devices described above, are often attached to the flexible tubing that interconnects the syringe to the source of water. The device described in U.S. Pat. No. 5,204,004, for example, is interposed in the flexible tubing through the use of Luer fittings. Unfortunately, such an arrangement may not satisfactorily reduce the amount of biofilm that may ultimately develop in areas downstream of the device including in areas of the various passages within the syringe.

Other suggestions in the past have included water purification devices that are connected directly to the air-water syringe. For example, U.S. Pat. No. 5,474,451 describes in certain embodiments a purifying device that is connected to a hand piece of a dental air-water syringe and in other embodiments a purifying device that is connected to a tip of the dental air-water syringe. Both such concepts are advantageous over the previously mentioned approach, in that the purifying device is relatively close to the location where the water is dispensed from the syringe and is downstream of the flexible tubing that interconnects the syringe and the source of water.

However, there remains a need in the art for a dental air-water syringe with a water purifying device that enhances maneuverability of the syringe tip in the patient's oral cavity. Preferably, the tip of such an air-water syringe would be readily detachable from the hand piece of the syringe for disposal and replacement or re-sterilization. Moreover, the water purifying device of such a syringe preferably would be relatively inexpensive in order to enhance the economic feasibility of disposing of the device after use on a single patient.

SUMMARY OF THE INVENTION

The present invention is directed in one embodiment toward a dental air-water syringe that comprises an elongated handle having an air passageway, a water passageway and at least one valve for controlling the flow of air and water through the air passageway and water passageway respectively. The handle includes a first coupler. The air-water syringe also has a tip that includes an elongated housing extending in a direction at a non-zero angle less than 180 degrees relative to the longitudinal axis of the handle. The housing has a first end portion and a second end portion. The housing includes an air conduit and a water conduit. The first end portion includes at least one air discharge port and at least one water discharge port for discharging air and water respectively directly into the patient's oral cavity. The housing contains a device for purifying water flowing through the water conduit. The housing includes a second coupler that releasably engages the first coupler for detachably connecting the tip directly to the handle.

The present invention is also directed in another embodiment to a dental air-water syringe that includes an elongated handle having an air passageway, a water passageway and at least one valve for controlling the flow of air and water through the air passageway and the water passageway respectively. The dental air-water syringe also has a tip that includes an elongated housing extending in a direction at a non-zero angle less than 180 degrees relative to the longitudinal axis of the handle. The housing includes an air conduit and a water conduit and has a certain transverse cross-sectional area along the majority of its length. The air-water syringe also includes a device for purifying water flowing through the water conduit. The device includes an elongated covering having a transverse cross-sectional area along the majority of its length that is approximately the same as the transverse cross-sectional area of the tip. The device and the tip are detachably connected to the handle.

These and other aspects of the invention are described in more detail below and are illustrated in the accompanying drawings.

BRIEF DESCRIPTION OF THE DRAWINGS

FIG. 1 is a front, top and left side perspective view of a dental air-water syringe in accordance with one embodiment of the present invention, wherein a tip of the syringe is shown as detached from a handle of the syringe;

FIG. 2 is a rear elevational view of a portion of the handle of the syringe shown in FIG. 1;

DETAILED DESCRIPTION OF THE PREFERRED EMBODIMENTS

Figure 3:
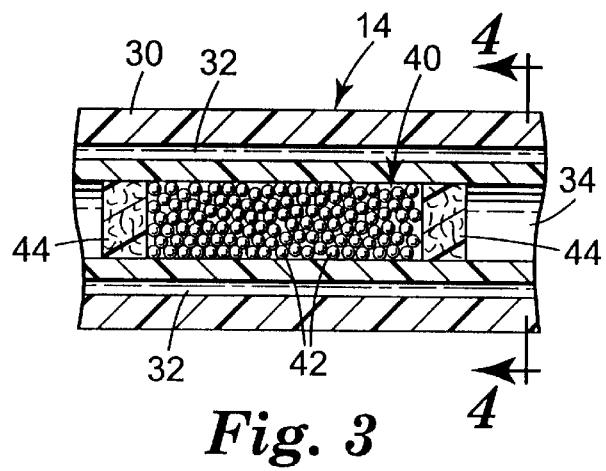
FIG. 3 is an enlarged side cross-sectional view of a portion of the syringe tip illustrated in FIG. 1.

A dental air-water syringe is designated by the numeral 10 in FIG. 1 and broadly includes a handle 12 and a tip 14. The handle 12 is elongated and has a somewhat frustroconical grip 16 that is connected at its upper end to a box-like head 18. The head 18 contains an air valve 20 and a water valve 22, both of which are of the normally off, push-button type and are typically operated by the user's thumb while the fingers are engaged around the grip 16.

A length of flexible, small-diameter air tubing 24 and a length of flexible, small-diameter water tubing 26 extend through an inner cavity of the handle 12 and are coupled to the air valve 20 and the water valve 22 respectively. The portion of the air tubing 24 that is external to the handle 12 is connected at its opposite end to a source of pressurized air (such as oil-free, filtered air from an air compressor), and the portion of the water tubing 26 that is external to the handle 12 is connected to a pressurized source of water (such as tap water). The air and water tubings 24, 26 extend in side-by-side relation and are preferably covered by a flexible sheath 28, a portion of which is illustrated in FIG. 1.

Figure 4:
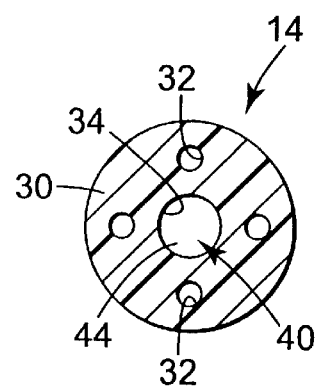
FIG. 4 is an enlarged end cross-sectional view of the syringe tip depicted in FIGS. 1 and 3 and taken along lines 4—4 of FIG. 3.

The tip 14 that is shown in FIG. 1 is illustrated in more detail and in enlarged form in FIGS. 3 and 4. The tip 14 includes an elongated housing 30 that contains at least one air conduit 32 and at least one water conduit 34. In the embodiment shown in the drawings, one water conduit 34 is provided and is centrally located along the central, longitudinal axis of the tip 14. The embodiment illustrated in FIGS. 3–4 also has four air conduits 32 that are equally spaced apart at 90 degree intervals around the water conduit 34 as can be appreciated by comparing FIG. 4 with FIG. 3. However, other constructions and configurations are also possible.

The housing 30 has a first, distal end portion and a second end portion that is connected to the handle 12. The air and water conduits 32, 34 extend from the second end portion to the first end portion. The first end portion includes at least one air discharge port and at least one water discharge port that communicate with the air conduits 32 and the water conduit 34 respectively. The water ports are adapted to dispense water directly into the patient's oral cavity in a narrow, concise stream in order to facilitate application of the water to the selected location. Moreover, a portion of the tip 14 is curved along its longitudinal axis at an acute angle to enhance spraying the air or water streams in the oral cavity.

The second end portion of the housing 30 includes an enlarged bell-shaped coupler 36 as shown in FIG. 1. Additionally, the handle 12 has a coupler 37 (FIG. 2) that matingly engages the coupler 36 for detachably connecting the tip 14 to the handle 12. In the embodiment illustrated, the coupler 36 has a pair of bayonet-style passages 38 (only one is shown) that receive respective outwardly extending pins of the coupler 37 for releasably locking the tip 14 to the handle 12 when the tip 14 is pivoted about its central, longitudinal axis. Of course, other types and styles of couplers are also possible including couplers having threaded portions and/or lock rings, Luer-type couplers, as well as friction fit couplers (e.g., with protruding tubular connectors that mate with o-ring receptacles).

The head 18 includes an air passageway and a water passageway that extend from the valves 20, 22 respectively toward a location adjacent the coupler 37 of the handle 12. The coupler 36 of the tip 14 has a fitting that communicates that air passageway in the head 18 with the air conduit 32 and the water passageway in the head 18 with the water conduit 34 whenever the tip 14 is connected to the handle 12.

The fitting in the coupler 36 is not shown in the drawings but can be of any suitable construction that provides an essentially leak-free path between the air passageway and the air conduit 32 and the water passageway and the water conduit 34 when the tip 14 in connected to the handle 12. Examples of suitable fittings are shown, for example, in U.S. Pat. Nos. 5,192,206 and 5,306,146 and EP 2 213 732. Optionally, the fitting is permanently secured within the coupler 36 in order to facilitate attachment of the tip 14 to the handle 12.

The housing 30 contains a water purifying device 40 that is shown in FIGS. 3 and 4. Preferably, the water purifying device 40 comprises a plurality of disinfecting iodide resin beads 42 that results in microbial kill in water passing through the water conduit 34. An example of suitable iodide beads 42 is described in Example II of U.S. Pat. No. 3,923,665.

The water purifying device 40 also includes a pair of porous plugs 44 located in the water conduit 34. The plugs 44 have a porosity that is sufficiently large to enable the flow of water therethrough without undue hindrance, and yet is sufficiently small to retain all of the beads 42 in the space between the plugs 44. The plugs 44 may be made of any suitable material such as a non-woven polypropylene, a screen mesh or other porous structure.

The water purifying device 40 with the iodide resin beads 42 is presently preferred because the beads 42 are relatively inexpensive and do not unduly restrict the flow of water passing through the water conduit 34. However, other types of water purifying devices are also possible. Examples include filters and devices that slowly release relatively low concentrations of a chemical disinfectant in the passing water.

The air-water syringe 10 that is illustrated in FIGS. 1–4 is an advantage in that the tip 14 has a relatively small outer diameter and yet entirely contains the water purifying device 40. Advantageously, the outer diameter of the tip 14 is relatively small and uniform along its entire length (except for the coupler 36). As an example, the outer diameter of the tip along its length is less than about 8 mm, more preferably less than about 6 mm and most preferably about 3 mm. Such construction facilitates maneuvering the tip 14 within the patient's oral cavity and also enhances the practitioner's view of the oral cavity when the tip 14 is present. Moreover, containment of the water purifying device 40 within the tip 14 ensures that the device 40 will not become unintentionally detached from remaining components of the tip 14 during the dental procedure.

Further, the embodiment shown in FIGS. 1–4 is relatively inexpensive to manufacture and thus is affordable for use on a single patient. Disposal of the tip 14 after a single use substantially reduces the likelihood that infectious disease will be transmitted from one patient to another. The housing 30 could be made of metal or plastic material although plastic is presently preferred due to its relatively low cost. An example of a suitable plastic material is injection-molded polyethylene or polypropylene.

Figure 5:
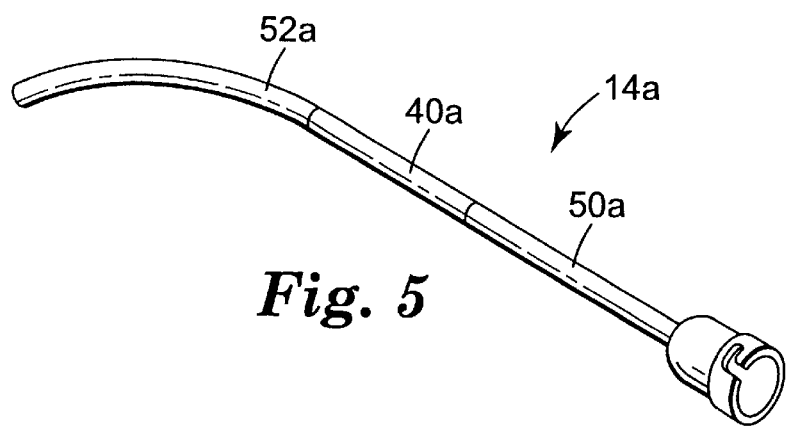
Fig. 5 is a perspective view of a tip for a dental air-water syringe in accordance with another embodiment of the present invention.
Figure 6:
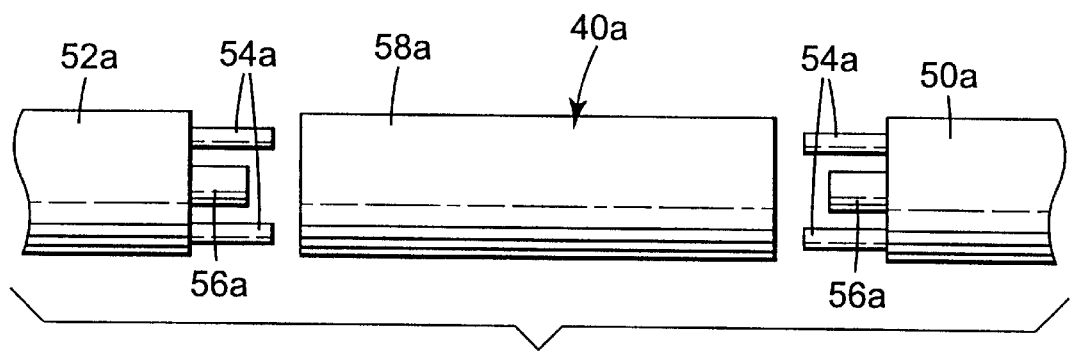
FIG. 6 is an enlarged, exploded, side elevational view of a portion of the tip depicted in FIG. 5.

The embodiment of the invention that is illustrated in FIGS. 5 and 6 concerns a dental air-water syringe having a tip 14a that is detachably connected to a handle. The handle is not shown in the drawings, but is optionally identical to the handle 12 illustrated in FIGS. 1–2. Moreover, the tip 14a and the handle are releasably connected together by mating couplers that are similar to the couplers described above and in connection with the embodiment shown in FIGS. 1–4.

The tip 14a includes a first section 50a that is normally located next to the handle and includes the coupler. The tip 14a also includes a second section 52a that is remote from the first section 50a. The second section 52a has at least one air discharge port and at least one water discharge port for discharging air and water respectively directly into the patient's oral cavity. A water purifying device 40a is interposed between the first and second sections 50a, 52a and is releasably connected to the same.

The first and second sections 50a, 52a each include a housing 30a with a pair of internal air conduits and a single water conduit although other configurations are also possible. The end portions of the first and second sections 50a, 52a that are adjacent the water purifying device 40a have a tubular, protruding air conduit coupling 54a and a protruding, tubular water conduit coupling 56a. The couplings 54a, 56a are received in friction-fit relation in mating passageways of the water purifying device 40a.

Preferably, the water purifying device 40a includes iodine resin beads similar to the beads 42 shown in FIG. 3. However, other types of water purifying structure such as filters or chemical disinfectants may also be employed.

The water purifying device 40a has an outer covering 58a with a cylindrical shape. Preferably, the outer diameter of the covering 58a is identical to the outer diameter of the first and second sections 50a, 52a (not including the portion of the first section 50a that encompasses the coupler). The water purifying device 40a is elongated and extends in coaxial relation with the first and sections 50a, 52a. Optionally, the water purifying device could be located in the curved portion of the tip 14a.

Other constructions are also possible. For example, the water purifying device 40a could include a curved portion and replace the first section 50a. As another option, the water purifying device 40a could include a coupler and replace the second section 52a. In all such constructions, however, the covering of the water purifying device presents a transverse cross-sectional area (as determined by measurement of its peripheral dimensions) along the majority of its length that is approximately the same as the transverse cross-sectional area of the housing along the majority of its length, so that maneuverability of the tip 14a in the oral cavity is facilitated. Advantageously, the syringe handle is preferably not modified and the couplings on the syringe can remain the same as presently manufactured couplings when a tip according to the present invention is employed.

EXAMPLES

Iodide resin beads were prepared according to Example II of U.S. Pat. No. 3,923,665. A Pro-Tip brand air-water syringe tip (from Sultan) was modified for the experiment. The modification included removal and shortening of an insert contained within a housing of the tip and then replacement of the insert.

Iodide beads were secured inside a length of polyethylene rubber tubing by use of a pair of polypropylene non-woven stoppers at each end of the tubing. The tubing had an internal diameter of 2.5 mm and the iodide beads filled a space having a length of about 1 cm within the tubing.

An overnight culture of Pseudomonas aeruginosa was grown in Nutrient Broth solution (from Difco Laboratories) at 37 degrees Centigrade. The culture was centrifuged, the media decanted and the culture (in the form of a pellet) was resuspended in an equal volume of sterile distilled water with 10% Nutrient Broth solution. The optical density at 600 nm was measured and the culture was diluted to approximately $1 \times 10^5$ Colony Forming Units per ml ("CFU"), based on the general relationship that an optical density ("OD") of 1.000 is equal to about $8.8 \times 10^8$ CFU per ml. A fresh dilution of the bacterial culture was made prior to each experiment.

The modified syringe tip as described above was connected to an ADEC brand air-water syringe using a Sultan Pro-Tip brand adapter. The air-water syringe was connected to a peristaltic pump (No. 7523-20, from Cole Parmer). The pump was adjusted to deliver 10 ml/min. The system was filled with diluted bacterial culture.

A total of 50 ml was pumped through the syringe tip. A 0.7 ml sample was collected after 10 ml. The samples and a control were then plated on Brain Heart Infusion agar (also known as BHI plates from DiMed Corp.) in triplicate using a spiral plater (model no. 3000, from SpiralTech). The plates were counted and the colony forming units per ml ("CFU/ml") of sample were determined after 18 hours incubation at 37 degrees Centigrade.

A second experiment was performed by again passing 50 ml of diluted bacterial culture through the same modified syringe tip as described above, except that in this experiment the flow rate through the tip was 39 ml/min. Samples were again taken after each 10 ml and plated as described above.

Results of the experiments are shown in the following table:

| Flow Rate ml/min | Sampling Designation (in sequential order) | CFU/ml Sample | | | | |
|---|---|---|---|---|---|---|
| 10 | Control | 7.69E + 04 | 6.66E + 04 | 5.13E + 04 | 6.49E + 04 | 1.29E + 04 |
| 10 | 1 | 0.00E + 00 | 0.00E + 00 | 0.00E + 00 | 0.00E + 00 | 0.00E + 00 |
| 10 | 2 | 0.00E + 00 | 0.00E + 00 | 0.00E + 00 | 0.00E + 00 | 0.00E + 00 |
| 10 | 3 | 0.00E + 00 | 0.00E + 00 | 0.00E + 00 | 0.00E + 00 | 0.00E + 00 |
| 10 | 4 | 0.00E + 00 | 0.00E + 00 | 0.00E + 00 | 0.00E + 00 | 0.00E + 00 |
| 10 | 5 | 0.00E + 00 | 0.00E + 00 | 0.00E + 00 | 0.00E + 00 | 0.00E + 00 |
| 39 | Control | 1.02E + 05 | 9.23E + 04 | 1.15E + 05 | 1.04E + 05 | 1.30E + 04 |
| 39 | 1 | 0.00E + 00 | 0.00E + 00 | 0.00E + 00 | 0.00E + 00 | 0.00E + 00 |
| 39 | 2 | 0.00E + 00 | 0.00E + 00 | 0.00E + 00 | 0.00E + 00 | 0.00E + 00 |
| 39 | 3 | 0.00E + 00 | 0.00E + 00 | 0.00E + 00 | 0.00E + 00 | 0.00E + 00 |
| 39 | 4 | 0.00E + 00 | 0.00E + 00 | 0.00E + 00 | 0.00E + 00 | 0.00E + 00 |
| 39 | 5 | 0.00E + 00 | 0.00E + 00 | 0.00E + 00 | 0.00E + 00 | 0.00E + 00 |

The data shows that the iodide resin beads killed all of the measurable microbes in water passing through the modified syringe tip in each of the 10 ml samples, even though the syringe tip is relatively compact and sufficiently small to provide enhanced maneuverability and visibility during use.

We claim:

1. A dental air-water syringe comprising:

an elongated handle having an air passageway, a water passageway and at least one valve for controlling the flow of air and water through the air passageway and the water passageway respectively, the handle including a first coupler; and a tip including an elongated housing extending in a direction at a non-zero angle less than 180 degrees relative to the longitudinal axis of the handle, the housing having a first end portion and a second end portion, the housing including an air conduit and a water conduit, the first end portion including at least one air discharge port and at least one water discharge port for discharging air and water respectively directly into the patient's oral cavity, the housing containing a device for purifying water flowing through the water conduit, the housing including a second coupler releasably engaging the first coupler for detachably connecting the tip directly to the handle, and wherein the housing has a cross-sectional area that is uniform along its entire length.

2. A dental air-water syringe according to claim 1, wherein the housing has an outer diameter that is substantially uniform along its entire length.

3. A dental air-water syringe according to claim 1, wherein the housing is integrally made of a plastic material.

4. A dental air-water syringe according to claim 1, wherein the housing has a curved longitudinal axis.

5. A dental air-water syringe comprising:

an elongated handle having an air passageway, a water passageway and at least one valve for controlling the flow of air and water through the air passageway and the water passageway respectively, the handle including a first coupler; and a tip including an elongated housing extending in a direction less than 180 degrees relative to the longitudinal axis of the handle, the housing having a first end portion and a second end portion, the housing including an air conduit and a water conduit, the first end portion including at least one air discharge port and at least one water discharge port for discharging air and water respectively directly into the patient's oral cavity the housing containing a device for purifying water flowing through the water conduit, the housing including a second coupler releasably engaging the first coupler for detachably connecting the tip directly to the handle, wherein the device for purifying water includes a plurality of iodide beads disposed along the length of the water conduit.

6. A dental air-water syringe according to claim 5, wherein the water purifying device includes at least one porous plug for retaining the iodide beads in a certain location.

7. A dental air-water syringe according to claim 5, wherein the water conduit extends along a central longitudinal axis of the tip.

8. A dental air-water syringe comprising:

an elongated handle having an air passageway, a water passageway and at least one valve for controlling the flow of air and water through the air passageway and the water passageway respectively;

a tip including an elongated housing extending in a direction at a non-zero angle less than 180 degrees relative to the longitudinal axis of the handle, the housing including an air conduit and a water conduit and having a certain transverse cross-sectional area along the majority of its length; and a device for purifying water flowing through the water conduit, the device including an elongated covering having a transverse cross-sectional area along a majority of its length that is the same as the transverse cross-sectional area of the housing, and wherein the device and the tip are detachably connected to the handle.

9. A dental air-water syringe according to claim 8, wherein the tip includes at least one protruding tubular coupling for connecting to the device, the tubular coupling having a passage for water.

10. A dental air-water syringe according to claim 9, wherein the coupling is received in friction-fit relation in the device.

11. A dental air-water syringe according to claim 8, wherein the tip includes a first elongated section and a second elongated section, the first section including at least one air discharge port and at least one water discharge port, the second section being connected directly to the handle such that the device is located between the first section and the second section.

12. A dental air-water syringe according to claim 11, wherein the device, the first section and the second section each have substantially circular cross-sections along the majority of their lengths with approximately equal outer diameters.

13. A dental air-water syringe comprising:

an elongated handle having an air passageway, a water passageway and at least one valve for controlling the flow of air and water through the air passageway and the water passageway respectively;

a tip including an elongated housing extending in a direction less than 180 degrees relative to the longitudinal axis of the handle, the housing including an air conduit and a water conduit and having a certain transverse cross-sectional area along the majority of its length; and a device for purifying water flowing through the water conduit, the device including an elongated covering having a transverse cross-sectional area along a majority of its length that is approximately the same as the transverse cross-sectional area of the housing and wherein the device and the tip are detachably connected to the handle, wherein the device includes at least one iodide bead.

* * * * *